United States Patent [19]

Giometti et al.

[11] Patent Number: 5,895,911
[45] Date of Patent: Apr. 20, 1999

[54] GLASS CONTAINER BODY CHECK DETECTOR

[75] Inventors: Stephen M. Giometti, Horseheads; William J. Furnas, Elmira, both of N.Y.

[73] Assignee: Emhart Glass S.A., Cham, Switzerland

[21] Appl. No.: 09/010,439

[22] Filed: Jan. 22, 1998

[51] Int. Cl.$^6$ .................................................. G01N 9/04
[52] U.S. Cl. .................................. 250/223 B; 356/239.4; 209/526
[58] Field of Search .................. 250/223 B, 559.42, 250/559.43, 559.45; 356/239.4, 239.5; 209/524, 526

[56] References Cited

U.S. PATENT DOCUMENTS

| | | | |
|---|---|---|---|
| 5,637,864 | 6/1997 | Nicks et al. | 250/223 B |
| 5,729,340 | 3/1998 | Griesbeck et al. | 250/223 B |

*Primary Examiner*—Que T. Le
*Assistant Examiner*—Kevin Pyo
*Attorney, Agent, or Firm*—Spencer T. Smith

[57] ABSTRACT

A glass container body check detector is disclosed which comprises a conveyor for conveying glass containers in a predetermined direction to an inspection station, a rotator for rotating a glass container at the inspection station about the axis of the glass container, and an inspection assembly for detecting a check in the body of the rotating glass container. The inspection assembly includes a diffuse light source for directing diffused light at the sidewall of the rotating glass container in a direction perpendicular to the predetermined direction of conveyance of the glass container, a pair of angularly related directed light sources located above the rotating container for focusing light through the container into coincident vertical lines of light on the sidewall of the container, from the top of the bottle to the bottom of the container, and a linear array camera located above the rotating glass container and focused on the coincident lines of directed light.

3 Claims, 2 Drawing Sheets

GLASS CONTAINER BODY CHECK DETECTOR

BACKGROUND OF THE INVENTION

In the standard process for making glass containers, certain defects occur due to various process variances. Among these defects, checks are a common type of defect. A check is a crack in the glass that causes a structural flaw in the container. This flaw will likely lead to the container's failure during or after filling. Checks can occur in almost any location on the container. Checks in the finish area and the heel area are detected using several methods. The primary method is to use a directed light source on a specific location on the bottle. A light sensitive sensor is placed such that the check or crack will reflect the directed light into that sensor. Since finish and heel checks occur in repeatable, expected locations, this method works reliably.

Checks that occur in the sidewall area (body) of the container are less repeatable. The process variance that produces such a check, does not cause the check to occur in a repeatable expected location. These checks tend to be large cracks that are curved in shape. They can also be located anywhere on the sidewall of the container.

U.S. Pat. Nos. numbered 3,245,533, 4,399,357 and 4,664,525, disclose check detecting systems.

OBJECT OF THE INVENTION

It is accordingly an object of the present invention to detect body checks in a glass container.

Other objects and advantages of the present invention will become apparent from the following portion of this specification and from the accompanying drawings which illustrate in accordance with the mandate of the patent statutes a presently preferred embodiment incorporating the principles of the invention.

BRIEF DESCRIPTION OF THE PREFERRED EMBODIMENT

Figure 1:
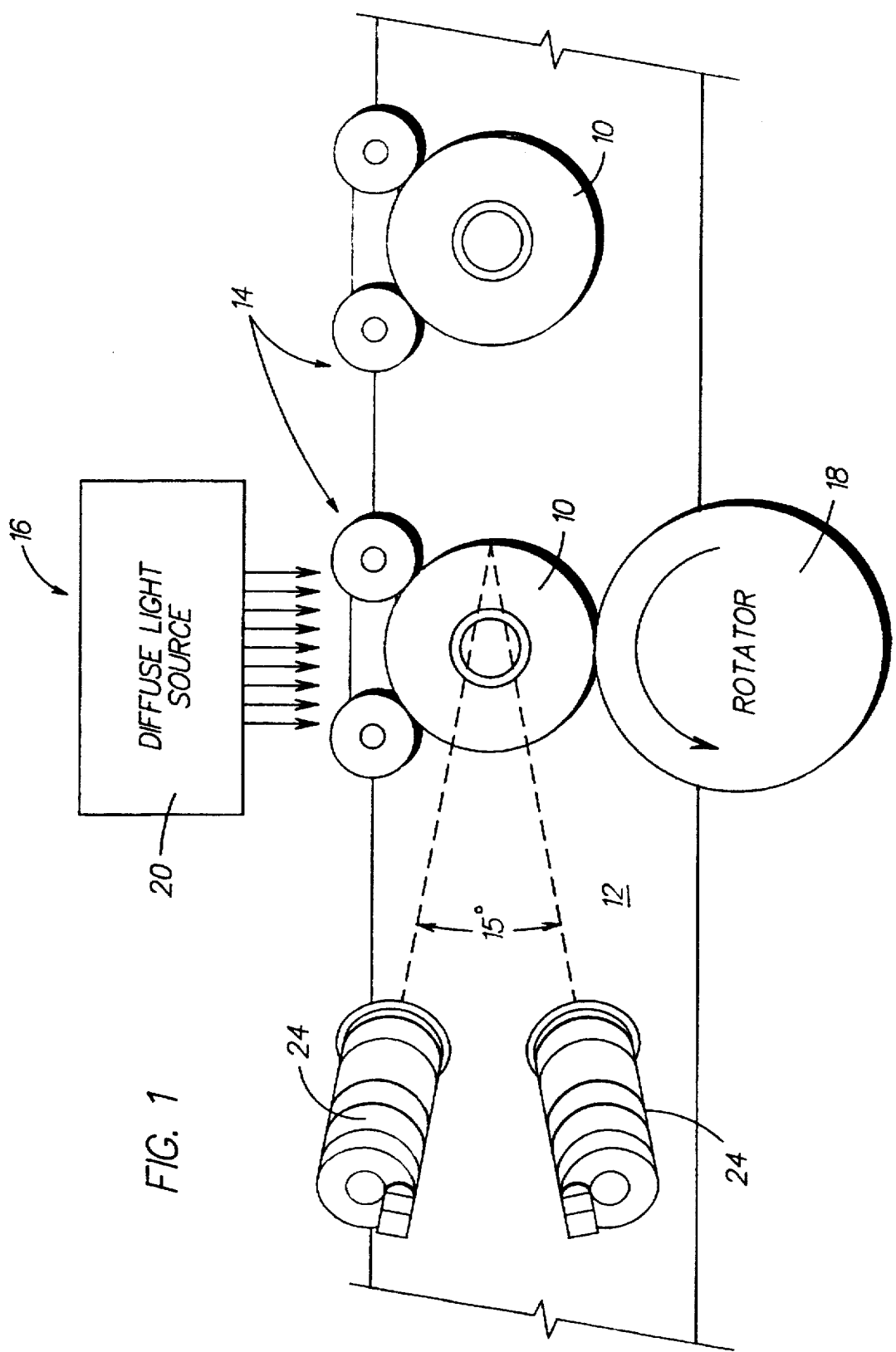
FIG. 1 is a top view of a portion of a glass container body check detector made in accordance with the teachings of the present invention.
Figure 2:
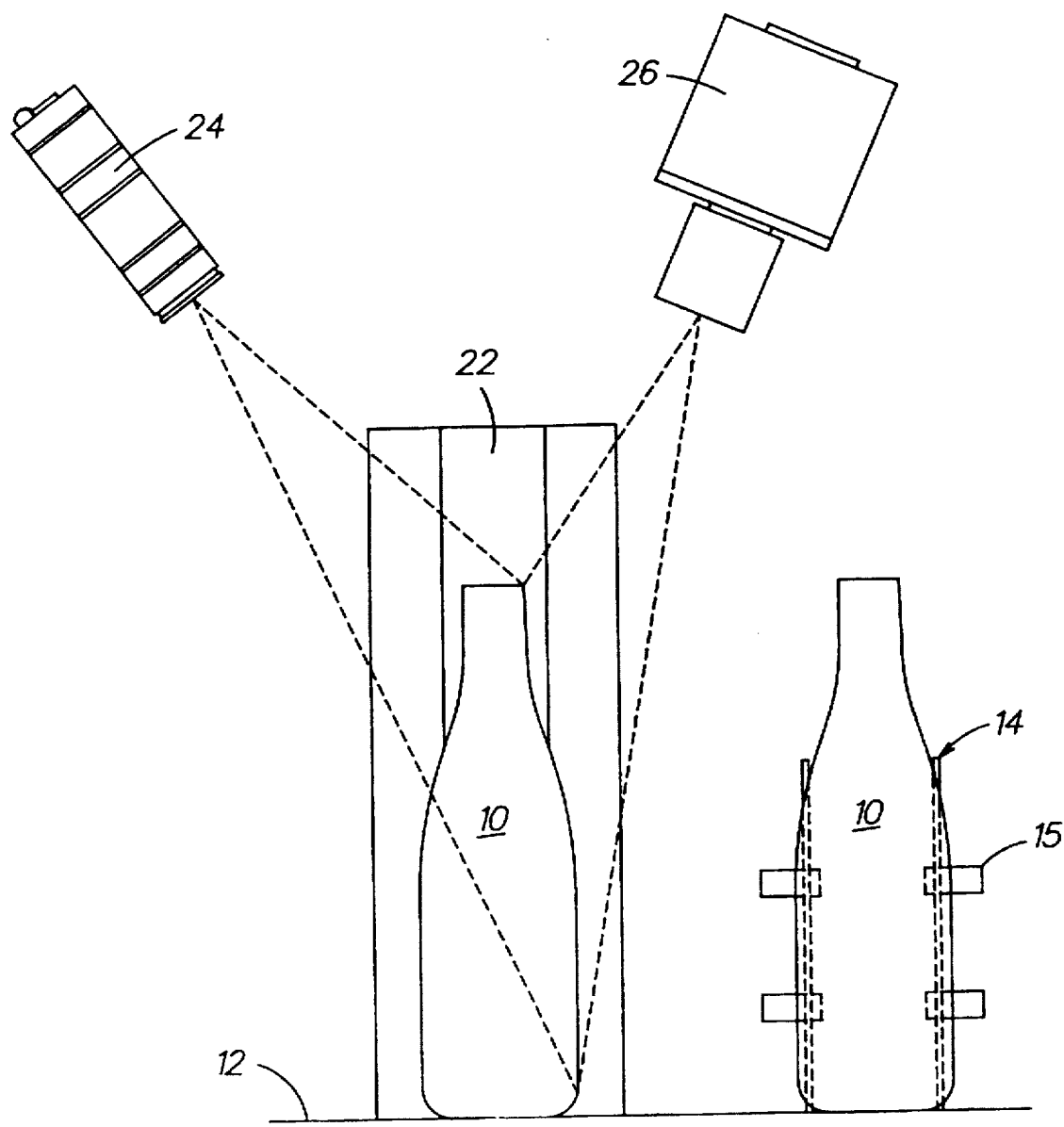
FIG. 2 is front view of a portion of the glass container body check detector shown in FIG. 1.

Glass containers 10 are transported along a conveyor 12 by suitable cars 14 which deliver the containers in sequence to an inspection station 16 where there is a dwell of sufficient duration that the glass container can be rotated by a rotator 18. A complete 360° inspection of the sidewall (body) of the container is made. The cars include upper and lower pairs of rollers 15 (FIG. 2) which engage the sidewall proximate the top and bottom (the cars have been deleted from the container at the inspection station for clarity).

The glass container is illuminated with two types of lighting. A diffuse light source 20 provides general lighting for the glass container. It includes a light source (not shown) and a diffuser panel 22. The light source may be an LED, incandescent or halogen light bulb array, for example. Two directed light sources 24, located above the glass containers, direct focused lines of light through the glass container. The light sources are aimed so that the focused lines will be coincident on the remote sidewall of the glass container being inspected extending from the top of the glass container down to the heel or bottom of the glass container. Each directed light source may be an incandescent bulb having a linear filament supported vertically so that a lens assembly can easily focus an image of the filament on the sidewall of the glass container. The two directed lights are placed at an angle of approximately 15° to each other with the lines of light focused on top of one another.

A linear array camera 26 is also mounted above the glass containers with the linear array supported in a vertical plane looking down at a sharp angle to see the coincident lines extending from the top to the bottom of the container (the linear array is focused on the coincident light lines) and to avoid the shadow of the adjacent bottle. The linear array is scanned to detect a check. The direction of the diffused light (perpendicular to the conveyor direction) and the location of the light sources is selected to create a dark field image for the linear array camera. Mirrors may be used to direct the image to the camera.

Only defects can cause light to leave the wall of the bottle and be reflected to the camera. The diffuse light source 20 provides general lighting for the container. Light travels to the check from many different directions. It will be refracted as it passes through the container side toward the check. Where the check is inclined to the vertical, light within the container will reflect off the internal surface of the check and travel up towards the camera. Where the check is horizontal (horizontal or almost horizontal), the general light will not be reflected from the check toward the camera. The light from the directed light sources will reflect off a horizontal check or check portion and be directed up to the camera.

We claim:

1. A glass container body check detector comprising a conveyor for conveying glass containers in a predetermined direction to an inspection station, rotator means for rotating a glass container at the inspection station about the axis of the glass container, inspection means for detecting a check in the body of the rotating glass container including a diffuse light source for directing diffused light at the sidewall of the rotating glass container in a direction perpendicular to the predetermined direction of conveyance of the glass container, a pair of angularly related directed light sources located above the rotating container for focusing light through the container into coincident vertical lines of light on the sidewall of the container, said vertical lines of light extending from the top of the container to the bottom of the container and the location of said coincident vertical lines on the container defining an angle with the location on the container where diffused light is striking the container, a linear array camera located above the rotating glass container and focused on the coincident lines of directed light, the angle between the coincident vertical light lines and the sidewall location where diffused light is striking the bottle and the location of the directed light sources above the rotating container being selected so that the image field will appear dark, inclined body checks will reflect the diffused light upwardly to said linear array camera and almost horizontal body checks will reflect directed light upwardly to said linear array camera.

2. A glass container body check detector according to claim 1, wherein said pair of angularly related directed light sources are separated by an angle of 15°.

3. A glass container body check detector according to claim 2, wherein the angle between the location of said coincident vertical lines on the container and the location where diffused light is striking the container is approximately 90°.

\* \* \* \* \*